(12) United States Patent
Marshall et al.

(10) Patent No.: US 9,517,309 B2
(45) Date of Patent: Dec. 13, 2016

(54) CONTROL OF PLUNGER POSITION IN AN INJECTION DEVICE

(71) Applicant: OWEN MUMFORD LTD, Oxfordshire (GB)

(72) Inventors: Jerry Marshall, Oxfordshire (GB); Jakub Tomaszewski, Oxfordshire (GB)

(73) Assignee: OWEN MUMFORD LTD., Oxfordshire (GB)

( * ) Notice: Subject to any disclaimer, the term of this patent is extended or adjusted under 35 U.S.C. 154(b) by 0 days.

(21) Appl. No.: 14/903,981

(22) PCT Filed: Jul. 2, 2014

(86) PCT No.: PCT/GB2014/052019
§ 371 (c)(1),
(2) Date: Jan. 8, 2016

(87) PCT Pub. No.: WO2015/004428
PCT Pub. Date: Jan. 15, 2015

(65) Prior Publication Data
US 2016/0151576 A1 Jun. 2, 2016

(30) Foreign Application Priority Data
Jul. 10, 2013 (GB) .................................. 1312387.2

(51) Int. Cl.
*A61M 5/00* (2006.01)
*A61M 5/315* (2006.01)
*A61M 5/20* (2006.01)

(52) U.S. Cl.
CPC ........... *A61M 5/31536* (2013.01); *A61M 5/20* (2013.01); *A61M 5/31551* (2013.01);
(Continued)

(58) Field of Classification Search
CPC ..................... A61M 5/31551; A61M 5/31501; A61M 5/31553
(Continued)

(56) References Cited

U.S. PATENT DOCUMENTS

| 7,169,131 B2 * | 1/2007 | Gatti ................. A61M 5/31553 604/187 |
| 2001/0009990 A1 * | 7/2001 | Hostettler ........... A61M 5/2066 604/209 |

(Continued)

FOREIGN PATENT DOCUMENTS

| WO | 2007/063342 A1 | 6/2007 |
| WO | 2011/114122 A1 | 9/2011 |

OTHER PUBLICATIONS

United Kingdom Search Report, dated Dec. 20, 2013, from corresponding GB Application.

(Continued)

*Primary Examiner* — Phillip Gray
(74) *Attorney, Agent, or Firm* — Young & Thompson (57) ABSTRACT

An injection device includes a housing, a receptacle for receiving a medicine cartridge and configured for attachment to a proximal end of the housing, and a leadscrew having an end for engaging with a bung of a cartridge. The leadscrew has a first thread extending axially along an outer surface thereof and at least one axially extending guide track. The injection device includes a rotatable drive mechanism for engaging with the first thread or guide track, and a guiding element for engaging with the other of the first thread or guide track, the guiding element being non-rotatable with respect to the housing during an injection operation, whereby rotation of the drive mechanism causes the leadscrew to move axially in a proximal direction in order to deliver a dose from the cartridge. The injection (Continued)

device further includes a stop member located proximal to the rotatable drive mechanism and the guiding element.

15 Claims, 10 Drawing Sheets

(52) U.S. Cl.
CPC .... *A61M 5/31553* (2013.01); *A61M 5/31583* (2013.01); *A61M 5/31593* (2013.01); *A61M 2005/31508* (2013.01); *A61M 2005/31516* (2013.01)

(58) Field of Classification Search
USPC .......................................... 604/209, 211, 224
See application file for complete search history.

(56) References Cited

U.S. PATENT DOCUMENTS

2001/0051792 A1* 12/2001 Kirchhofer ....... A61M 5/31553
604/209
2012/0283658 A1* 11/2012 Plumptre ................ A61M 5/24
604/211

OTHER PUBLICATIONS

International Search Report, dated Sep. 16, 2014, from corresponding PCT Application.

* cited by examiner

CONTROL OF PLUNGER POSITION IN AN INJECTION DEVICE

TECHNICAL FIELD

The present invention relates to injection devices for delivering a dose of medicine to a user from a cartridge containing medicine, and more particularly to injection devices having a mechanism for accurately controlling the plunger position.

BACKGROUND

Injection devices are routinely used in the medical field to deliver a measured dose of medicine to a user. Due to their user-friendly design, they can be safely used by patients for self-administration, although in some circumstances they may be used by trained medical personnel.

Figure 1:
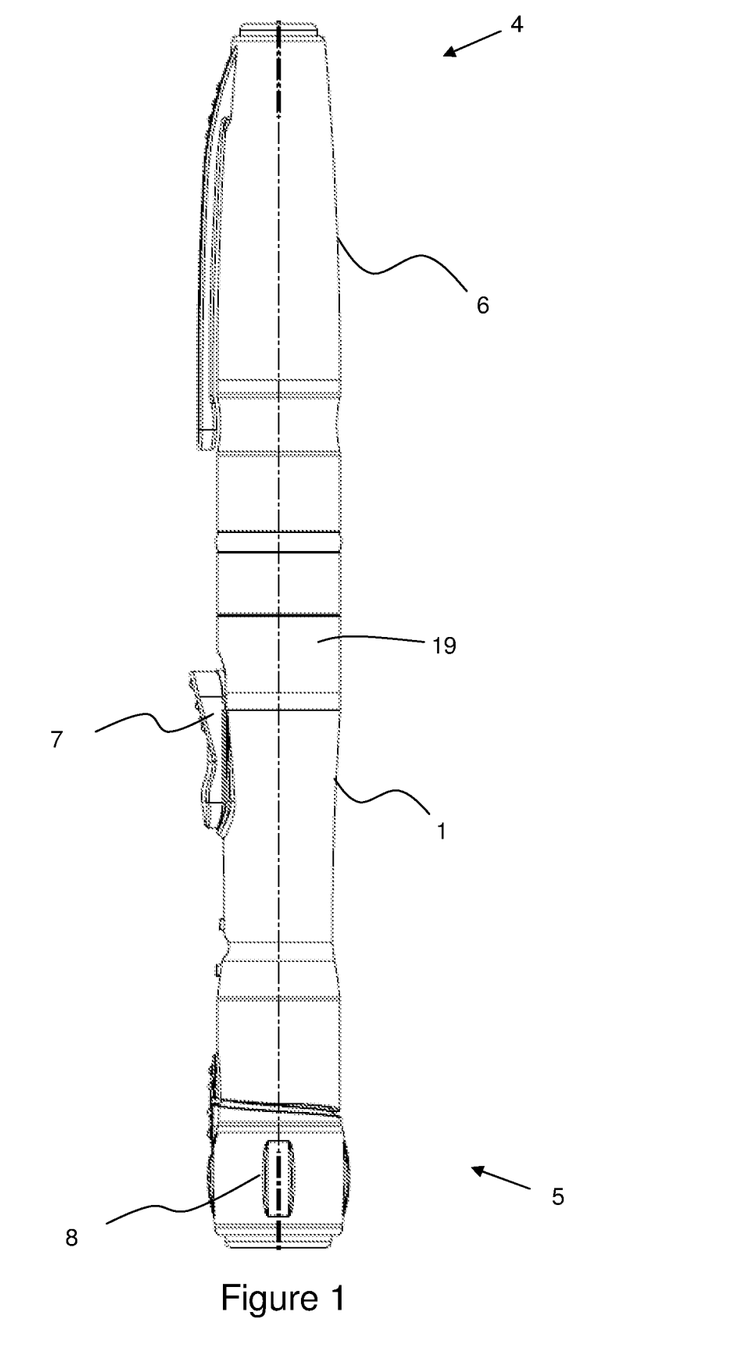
FIG. 1 illustrates schematically an external view of a prior art pen injector.
Figure 2:
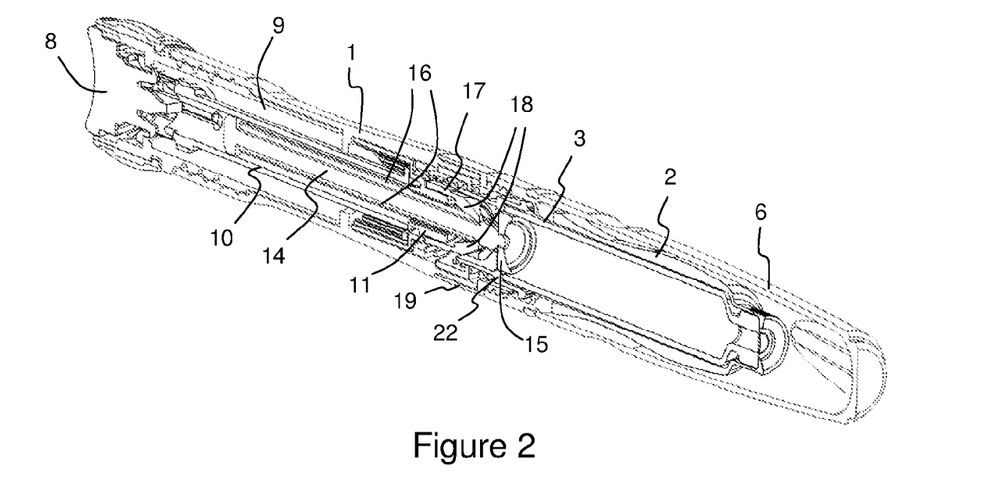
FIG. 2 illustrates schematically a cross-sectional view of the prior art pen injector of FIG. 1 in a fully reset configuration.
Figure 3:
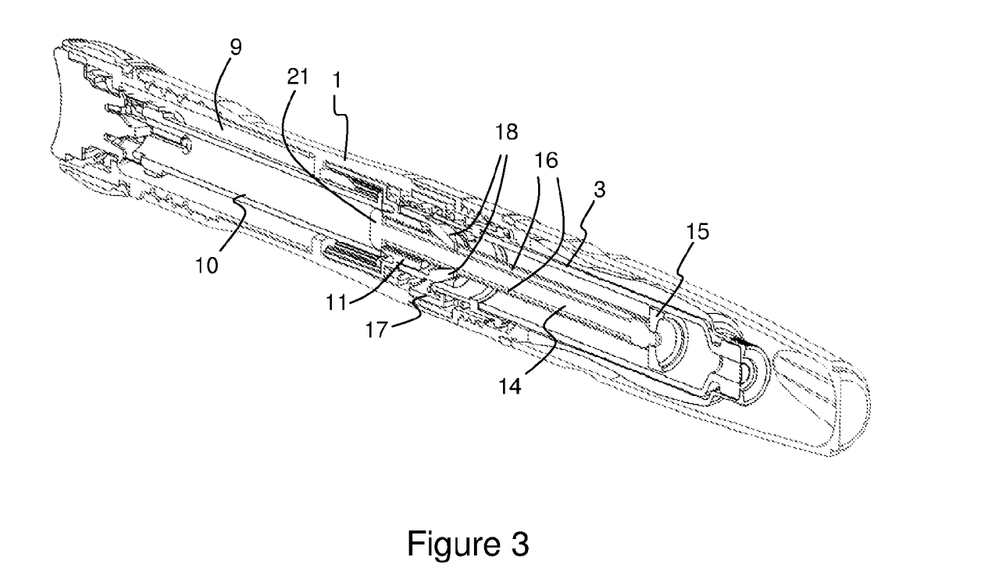
FIG. 3 illustrates schematically a cross-sectional view of the prior art pen injector of FIG. 1 in a fully discharged configuration.
Figure 4:
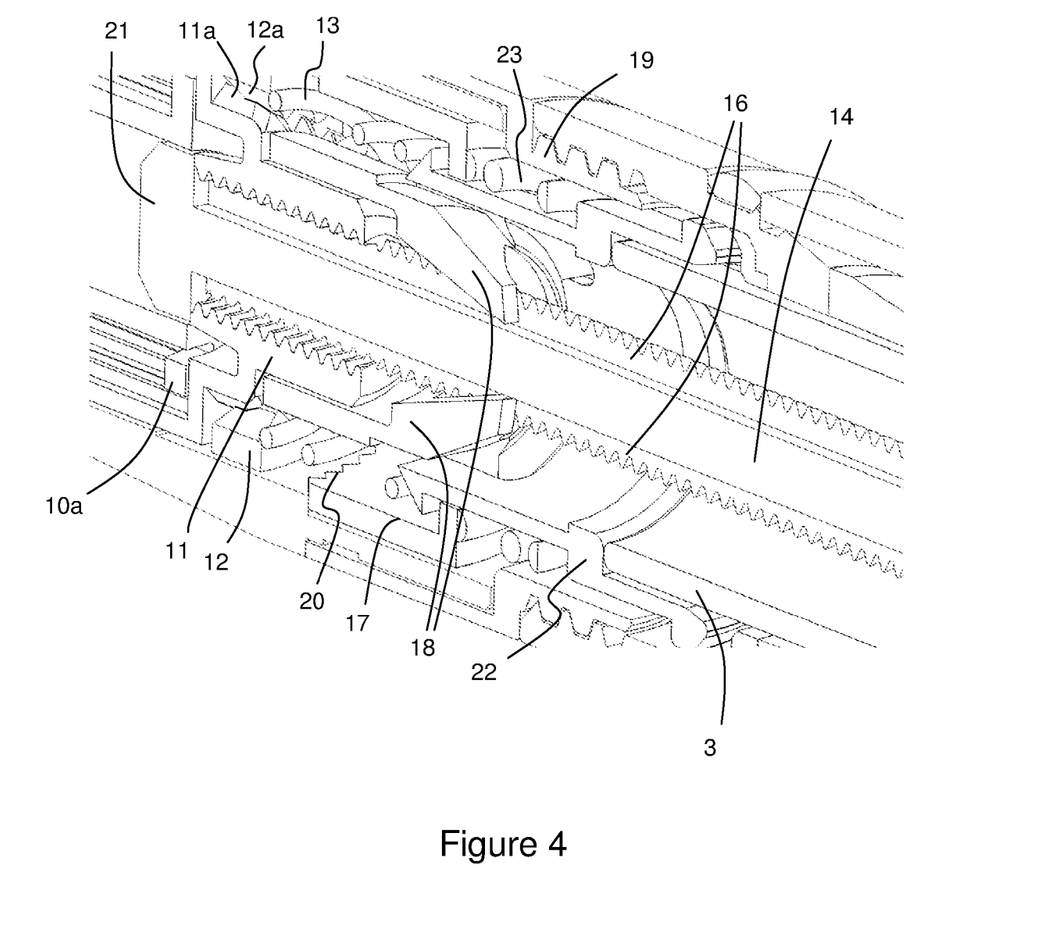
FIG. 4 illustrates an enlarged portion of the prior art pen injector in the configuration of FIG. 3.

A typical injection device comprises a relatively large number of parts. For example, FIGS. 1 to 4 illustrate schematically an OWEN MUMFORD AUTOPEN® device suitable for use with prefilled medicine cartridges, i.e. a device type commonly referred to as a "pen injector". A related description is provided in WO/2007/063342. FIG. 1 shows a side profile of the pen injector. FIG. 2 shows the pen injector in a fully reset configuration. FIG. 3 shows the pen injector in a fully discharged configuration. FIG. 4 provides an expanded view of a central section of the device.

With reference to FIGS. 1 to 4, the known pen injector comprises a housing 1 to which a receptacle 2 is connected. The receptacle 2 is arranged to receive the medicine cartridge 3. The pen injector has a cover 6 for protecting the receptacle 2 when not in use. The housing 1 is provided with a trigger 7 for actuating the device, and a dose knob 8 for selecting a dose. The housing 1 contains a torsion spring 9. The torsion spring 9 is located coaxially within the housing 1 and is arranged to provide a drive force for ejecting medicine from the cartridge 3.

A generally cylindrical ratchet drive shaft 10 extends through the centre of the torsion spring 9. An enlarged end portion 10a of the shaft 10, located at a proximal end, and has three sprung legs formed around its periphery, the legs being spaced equally around the shaft 10. At the outermost end of each leg, a tooth is provided. These teeth engage with a rack (not shown) formed around the inner surface of a drive gear 11, which sits within the housing 1 at a fixed axial position. The drive gear 11 has a second toothed rack 11a formed around a lower outer surface portion. The rack 11a sits within a correspondingly sized rack 12a formed on an inner surface of a retaining ring 12. The ring 12 is formed integrally with the trigger 7, with the trigger 7 being slidably mounted within a slot formed in the housing 1. A spring 13 urges the trigger 7 in a distal direction, maintaining the racks 11a and 12a in locking engagement in the absence of a user applied force.

A leadscrew 14 has a screw thread formed along the length of its outer surface. The leadscrew 14 is located within the ratchet drive shaft 10, and engages a complimentary screw thread formed on the inner surface of the drive gear 11. An end portion of the leadscrew projects from the ratchet drive shaft 10 and has a leadscrew cap 15 secured thereto. The cap 15 is rotationally attached to the leadscrew 14, such that it can be rotated relative to the leadscrew 14. The leadscrew 14 has axial guide tracks 16 extending along its outer surface and which engage with a locking bush 17 via splines 18 on the locking bush 17. The locking bush 17 is slidably held within a mid-body compartment 19 which itself is secured to the end of the housing 1 via a pair of complimentary screw threads. The locking bush 17 has a serrated edge 20 running along an end for engaging with mating features of the housing 1.

Consider now the operation of the pen injector. A user sets a dose by rotating the dose knob 8 in a clockwise direction. As the dose knob 8 is rotated, the distal end of the torsion spring 9 rotates with it, accumulating energy in the spring. Engagement of sprung fingers (not shown) at a distal end of the ratchet drive shaft 10 with a rack formed on the inner surface of the dose selector 8 also causes the ratchet drive shaft 10 to rotate. At a proximal end of the ratchet drive shaft 10, the teeth of the sprung legs "click" around the rack (not shown) formed around the inner surface of the drive gear. The engagement of the teeth with the rack at the proximal end of the ratchet drive shaft 10 prevents the spring 9 unwinding after each click. Each click corresponds to a predefined angular rotation of the spring and therefore to a predefined ejection dose. It will be readily appreciated that, during the dose setting action, the drive gear 11 is not rotated so no axial movement of the leadscrew 14 is induced. No medication is therefore ejected from the cartridge during the dose setting operation (or indeed air introduced due to back filling).

Once a dosage is set, the user can apply a force to the trigger 7 in the proximal direction. This disengages the rack 12a of the trigger 7 from the rack 11a of the drive gear 11. This frees the drive gear 11 and the torsion spring 9 to rotate. As the drive gear 11 rotates about the leadscrew 14, the leadscrew 14 is driven through the drive gear 11 causing the leadscrew cap 15 to push the bung of the cartridge 3 through the cartridge body, expelling medication from the cartridge 3 through an attached syringe.

The known pen injector is able to deliver several doses from the same medication filled cartridge 3. During delivery of each successive dose, the leadscrew 14 is advanced further forward into the medication filled cartridge 3. This continues until an enlarged end 21 of the leadscrew 14 engages with a distal end of the drive gear 11, at which point the leadscrew 14 has reached the end of its travel. FIG. 3 shows the known pen injector in this position.

During the injection process, the leadscrew 14 must be prevented from rotating relative to the housing 1. However, following the removal of the spent cartridge, it must be possible to push the leadscrew 14 back into the housing 1 to a starting position, this operation requiring rotation of the leadscrew within the housing. This is achieved by means of the locking bush 17.

Following removal of the receptacle from the housing, a spring 23 urges the locking bush 17 in the proximal direction relative to the housing, disengaging the locking bush from the housing and allowing it to rotate relative thereto. Once a new cartridge has been loaded into the receptacle 2, the user attaches the receptacle 3 onto the end of the housing 1. On coupling of the receptacle 2 to the housing 1, the leadscrew cap 15 abuts the bung in the end of the cartridge 3. The user pushes the receptacle 2 towards the housing 1, causing the leadscrew 14 to rotate within the drive gear 11 and move back into the housing 1. When the screw thread on the receptacle 2 engages with that on the housing 1, the user screws the two parts together, with the leadscrew 14 continuing to rotate and move into the housing 1 during this process.

On final coupling with the receptacle 2, the receptacle 2 and cartridge 3 engage with a cartridge compression cup 22, which compresses the spring 23 and transmits the loading onto the locking bush 17. The locking bush 11 re-engages with the housing, preventing the locking bush 17 from further rotation and also locking the leadscrew against rotation by means of the engagement of the splines 18 with the axial guide tracks 16. This ensures that the leadscrew 14 can move forward when subjected to rotation following release and rotation of the drive gear 11.

Medication filled cartridges are generally tubular in shape, although, due to structural considerations, have a slightly tapered portion towards the needle receiving end. If the bung is allowed to be pushed into this tapered end region there is a danger a) that the cartridge 3 may fracture and b) that an unreliable dose will be delivered (as the dosing mechanism assumes a uniform cartridge cross-section). Ideally, the device is configured such that the cap 15 cannot move beyond a point at which the bung is about to enter the tapered end portion of the cartridge 3. This is achieved by configuring the device such that the enlarged end 21 of the leadscrew 14 engages with a distal end of the drive gear 11 to stop the leadscrew, and therefore the bung, at the correct position relative to the cartridge. Of course, the configuration must take account of manufacturing tolerances, meaning that, in practice, the end 21 must be stopped at some distance distal from the "theoretical" stopping point, i.e. the device must be designed to provide a "buffer zone".

The buffer zone that must be incorporated into the device will depend upon the number of connected components. In the case of the device of FIGS. 1 to 4, the tolerance with which the stopping point of the end 21 can be defined depends upon the sum of the individual tolerances of the housing 1, receptacle 2, drive gear 11, mid-body compartment 19, and locking bush 17. This might be as much as 0.6 mm, meaning that on average the end of the bung will stop 0.6 mm distal from the desired stopping point in the cartridge. As a result, on average, a significant amount of medicine will remain in the cartridge 3 after a final injection from the cartridge. This has significant cost implications.

SUMMARY

It is an object of the present invention to reduce waste of medicine when using an injection device. This object is achieved by reducing the cumulative impact of manufacturing tolerances on the final stopping point of the bung within the medicine cartridge.

According to a first aspect of the present invention there is provided an injection device comprising a housing, a receptacle for receiving a medicine cartridge and configured for attachment to a proximal end of the housing, and a leadscrew having an end for engaging with a bung of a cartridge. The leadscrew has a first thread extending axially along an outer surface thereof and has at least one axially extending guide track. The injection device further comprises a rotatable drive mechanism for engaging with said first thread or said guide track and a guiding element for engaging with the other of said first thread or said guide track, the guiding element being non-rotatable with respect to the housing at least during an injection operation, whereby rotation of the drive mechanism causes said leadscrew to move axially in a proximal direction in order to deliver a dose from the cartridge. The injection device further comprises a stop member located proximal to said rotatable drive mechanism and said guiding element. The stop member is engaged with the or each guide track of said leadscrew to allow relative axial movement of the leadscrew and the stop member while causing the two components to rotate together, said stop member and a profile of the or each guide track being configured to define an end stop for the leadscrew in the proximal direction.

The present invention addresses problems associated with the cumulative impact of manufacturing tolerances on the final stopping point of a bung within a medicine cartridge. This is achieved by defining an end stop proximal to the rotatable drive member. As a result, the impact of manufacturing tolerance associated with the rotatable drive member on the final stopping point of the bung is greatly reduced. This allows a smaller buffer zone to be defined and, as a result, less medicine will remain in the cartridge after a final injection from the cartridge.

As an option the profile may comprise a step change in the depth of the or each guidetrack at an intermediate position, where the or each guide track has a first depth x in a proximal region of the leadscrew and a second depth y in a distal region, where x is greater than y.

As an option the stop member comprises at least one stop spline, where the or each stop spline is configured to engage with the or each guide track.

As an option the or each stop spline of the stop member extends a distance greater than y into the or each guide track.

In a first embodiment of the present invention the rotatable drive mechanism comprises a drive gear having a second thread provided on an inner surface thereof, the leadscrew and the drive gear being rotatably coupled by means of said first and second threads, and said guiding element is a locking bush located proximal to said drive gear and comprising one or more splines for engaging with the or each guide track of the leadscrew to allow relative axial movement of the leadscrew and the locking bush while preventing relative rotational movement. The locking bush is configured to allow rotation of the leadscrew when the receptacle is disconnected from the housing and to prevent rotation when the receptacle is connected to the housing. As an option the or each spline of the locking bush extends a distance less than y into the or each guide track.

As an option the first embodiment further comprises a cartridge compression cup, which is slidably mounted within the housing and is engagable by the receptacle during attachment of the receptacle to move said locking bush from a position in which it is rotatable with respect to the housing to a position in which it is non-rotatable, and wherein said stop member is located within said compression cup.

In a second embodiment of the present invention the rotatable drive mechanism comprises a drive collar comprising one or more splines for engaging with the or each guide track such that the drive collar and leadscrew rotate together, and the guiding element is a nut, said nut having a second thread on an inner surface thereof and the leadscrew and the nut being rotatably coupled by means of said first and second threads.

As an option the second embodiment further comprises a cartridge compression cup. The cartridge compression cup is slidably mounted within the housing and is engagable by the receptacle during attachment of the receptacle to move said nut from a position in which the nut is rotatable with respect to the housing to a position in which the nut is non-rotatable, and wherein said stop member is located within said compression cup. As an option the stop member is rotatable within said compression cup. As a further option the or each drive spline of the drive collar extends a distance less than y into the or each guide track.

As an option a proximal end position of the stop member is defined by abutment of the stop member with an attached cartridge.

As an option a torsion spring is coupled to the rotatable drive mechanism in order to rotate the drive mechanism within the housing.

As an option the stop member is a stop collar.

According to a second aspect of the present invention there is provided an injection device comprising a housing, a receptacle for receiving a medicine cartridge and configured for attachment to a proximal end of the housing, and a leadscrew having an end for engaging with a bung of a cartridge, the leadscrew having a first thread extending axially along an outer surface thereof and having at least one axially extending guide track. The injection device further comprises a drive gear having a second thread on an inner surface thereof, the leadscrew and the drive gear being rotatably coupled by means of said first and second threads, and a drive mechanism for causing relative rotation of said leadscrew and said drive gear in order to deliver a dose from the cartridge. The injection device further comprises a locking bush located proximal to said drive gear and being engaged with the or each guide track of the leadscrew to allow relative axial movement of the leadscrew and the locking bush while preventing relative rotational movement, the locking bush being configured to allow rotation of the leadscrew when the receptacle is disconnected from the housing and to prevent rotation when the receptacle is connected to the housing. The injection device further comprises a stop member located proximal to said locking bush and being engaged with the or each guide track of said leadscrew to allow relative axial movement of the leadscrew and the stop member while allowing the two components to rotate together, said stop collar and a profile of the or each guide track being configured to define an end stop for the leadscrew in the proximal direction.

DETAILED DESCRIPTION

An injection device of the pen injector type will now be described with respect to FIGS. 5 to 11. This device aims to provide better control over the stopping position of a plunger within the device, and hence of the bung within the cartridge, and thus reduce wasted medicine. The pen injector is described as an improvement vis-à-vis the device described in WO/2007/063342, and reference should be made to that document. However, the principles of the improvement can be applied to modifications of that device, and to pen injectors having other configurations. Reference below to a "proximal" end of the device refers to the end closest to the needle end, whilst reference to a "distal" end refers to the end furthest from the needle end. Proximal and distal directions are similarly defined.

With reference to FIGS. 5 to 11, an improved pen injector is illustrated, using like reference numerals to identify components common with the prior art device of FIGS. 1 to 4. The improved pen injector has a modified leadscrew 24, shown in FIG. 5. The leadscrew 24 features a step profile 25 in each of the axial guide tracks 26. The profile changes the depth of the track from a first depth x in a proximal region of the track (i.e. the region closest to the needle position) to a second depth y in a distal region (i.e. a region further from the needle position), where x is greater than y. As with the prior art device of FIGS. 1 to 4, the axial guide tracks 26 engage with a locking bush 27 via splines 28 of the locking bush 27. The splines 28 are configured to extend into the guide tracks to a depth just less than y such that the splines do not interfere with movement of the leadscrew 24 in the axial direction. As in the prior art device, the locking bush 27 acts to prevent rotation of the leadscrew 24 when the receptacle 2 and cartridge 3 are attached to the housing, whilst allowing rotation of the leadscrew 24 following removal of the receptacle 2 and prior to its complete reattachment.

Figure 5:
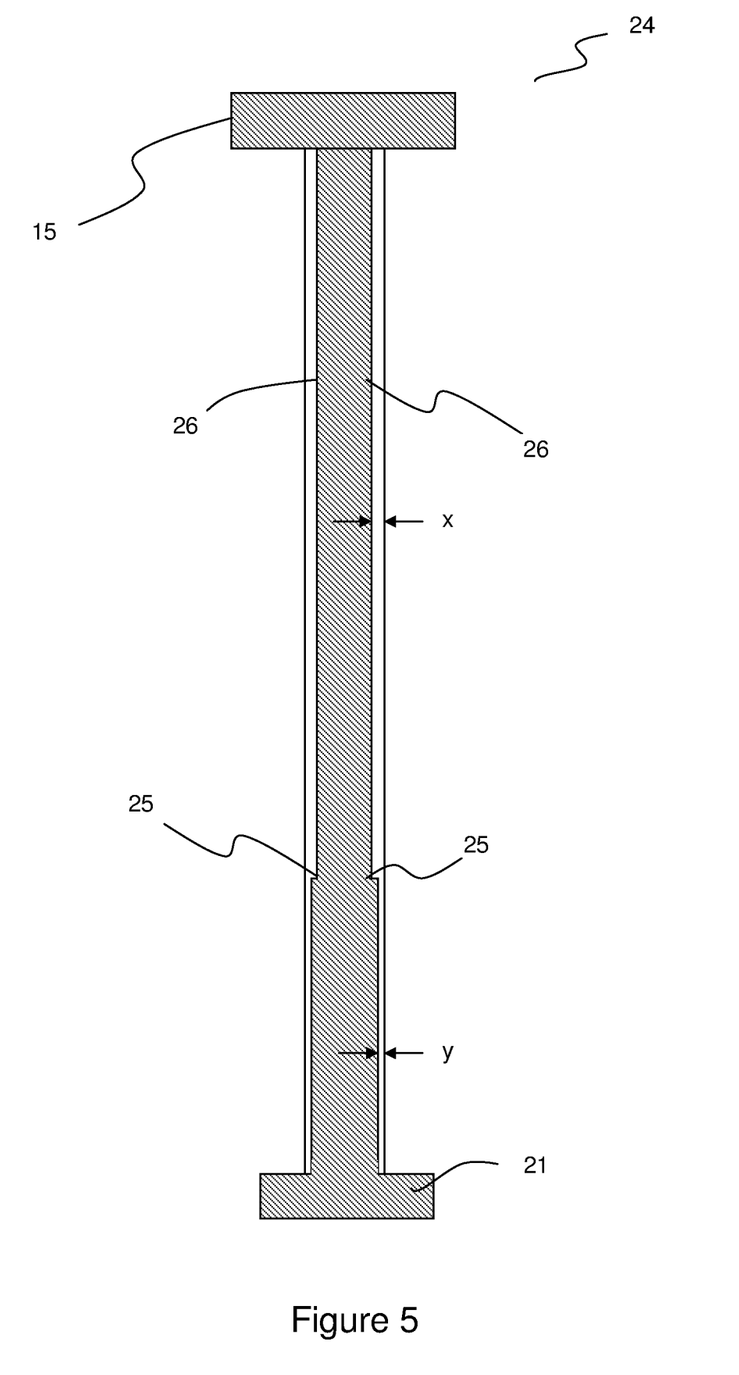
FIG. 5 illustrates schematically an axial cross-section through a modified leadscrew.
Figure 6:
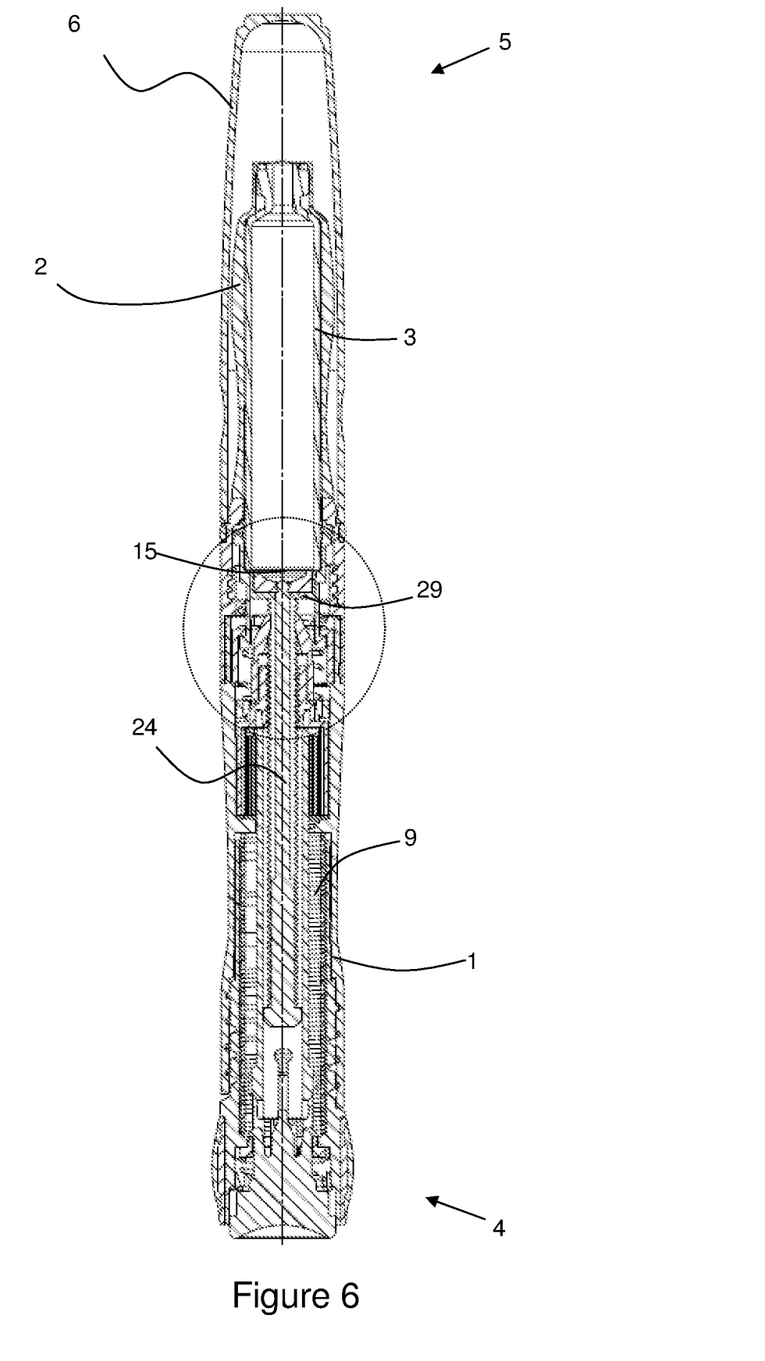
FIG. 6 illustrates schematically a cross-section through an improved pen injector in a fully reset configuration.
Figure 7:
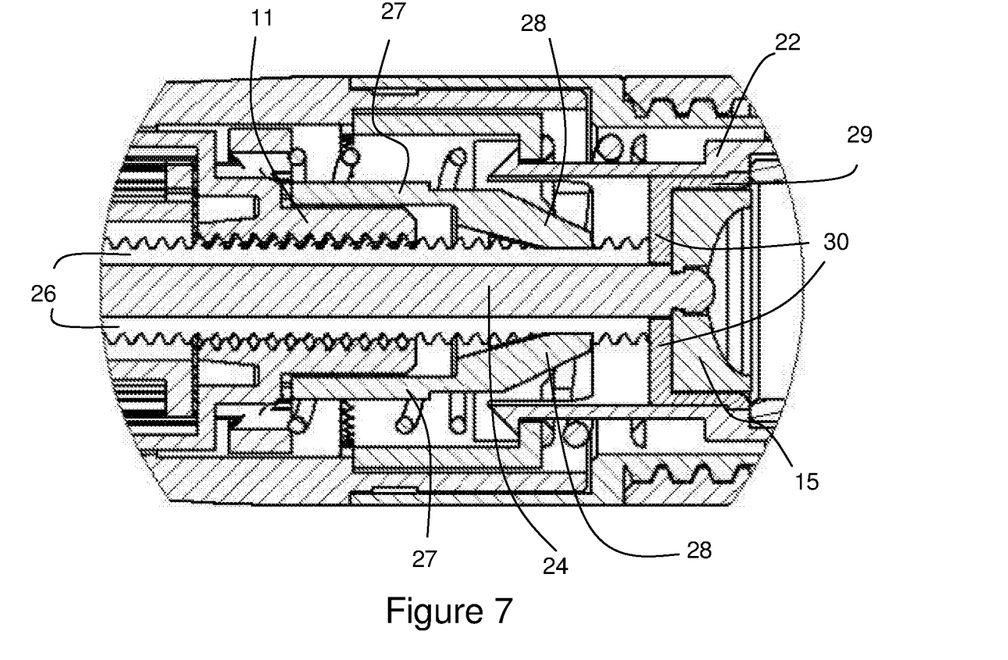
FIG. 7 illustrates schematically a portion of the improved pen injector in the configuration of FIG. 6.
Figure 8:
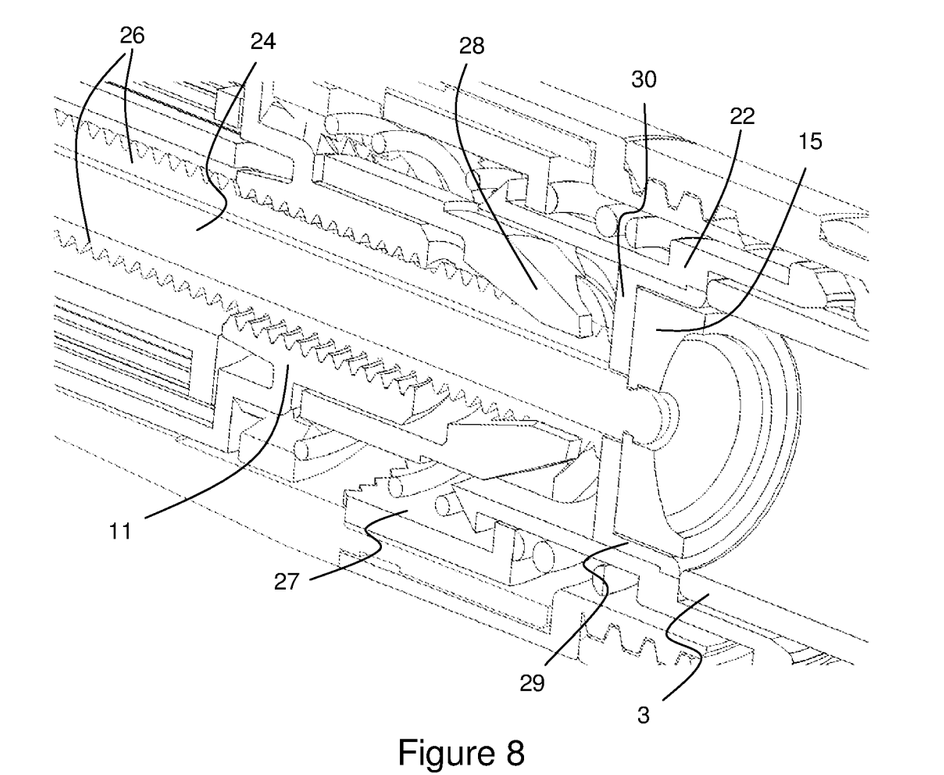
FIG. 8 illustrates schematically a portion of the improved pen injector in the configuration of FIG. 6.

The improved pen injector comprises a stop collar 29. The stop collar 29 has two stop splines 30 that engage with the axial guide tracks 26 in the leadscrew 24. The stop splines 30 project into the tracks 26 to a depth that is just less than x and greater than y. As such, the stop splines 30 allow the leadscrew 24 to move axially up to the point at which the stop splines 30 engage with the step profiles 25 in the guide tracks 26, at which point further axial movement of the leadscrew 24 in the proximal direction is blocked.

The stop collar 29 may be integrally formed with, or sit within, the cartridge compression cup 22. The stop collar 29 may define a seat to receive the cap 15 when in a fully reset configuration. This can be seen more clearly in FIG. 8. When the receptacle 2 is fully connected to the housing 1, the distal end of the cartridge 3 abuts the stop collar 29, restricting axially movement of the stop collar 29.

Consider now the operation of the improved pen injector. A user sets a dose by rotating the dose knob 8 in a clockwise direction. Once a dose is set and the needle inserted into the user's skin, the user can apply a force to the trigger 7 in the proximal direction in order to inject the medicine. This disengages the rack 12a of the trigger 7 from the rack 11a of the drive gear 11, in turn freeing the drive gear 11 to rotate under the influence of the torsion spring 9. As the drive gear 11 rotates about the leadscrew 24, the leadscrew 24 is driven through the drive gear 11 causing the leadscrew cap 15 to push the bung of the cartridge 3 through the cartridge body, expelling medication from the cartridge 3 through an attached needle.

Figure 9:
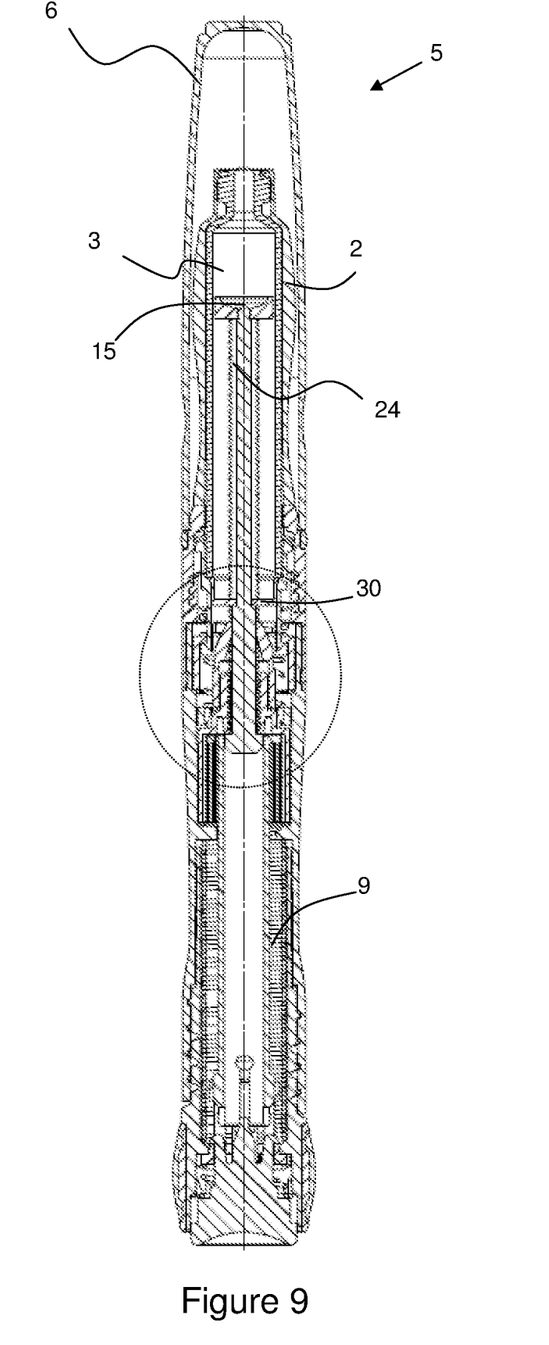
FIG. 9 illustrates schematically a cross-section through an improved pen injector in a fully discharged configuration.
Figure 10:
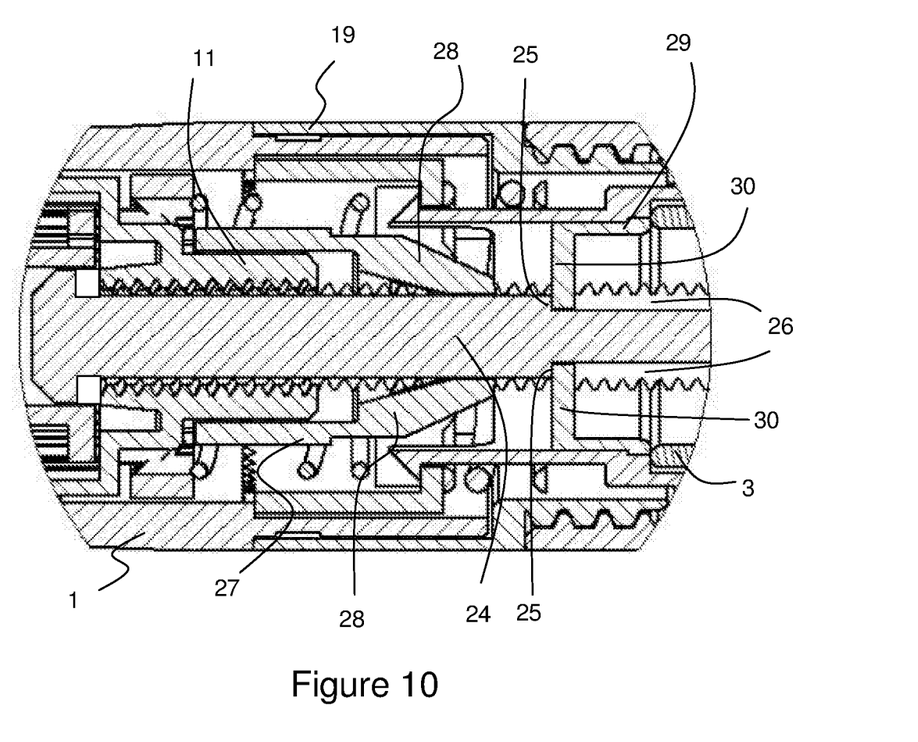
FIG. 10 illustrates schematically a portion of the improved pen injector in the configuration of FIG. 9.
Figure 11:
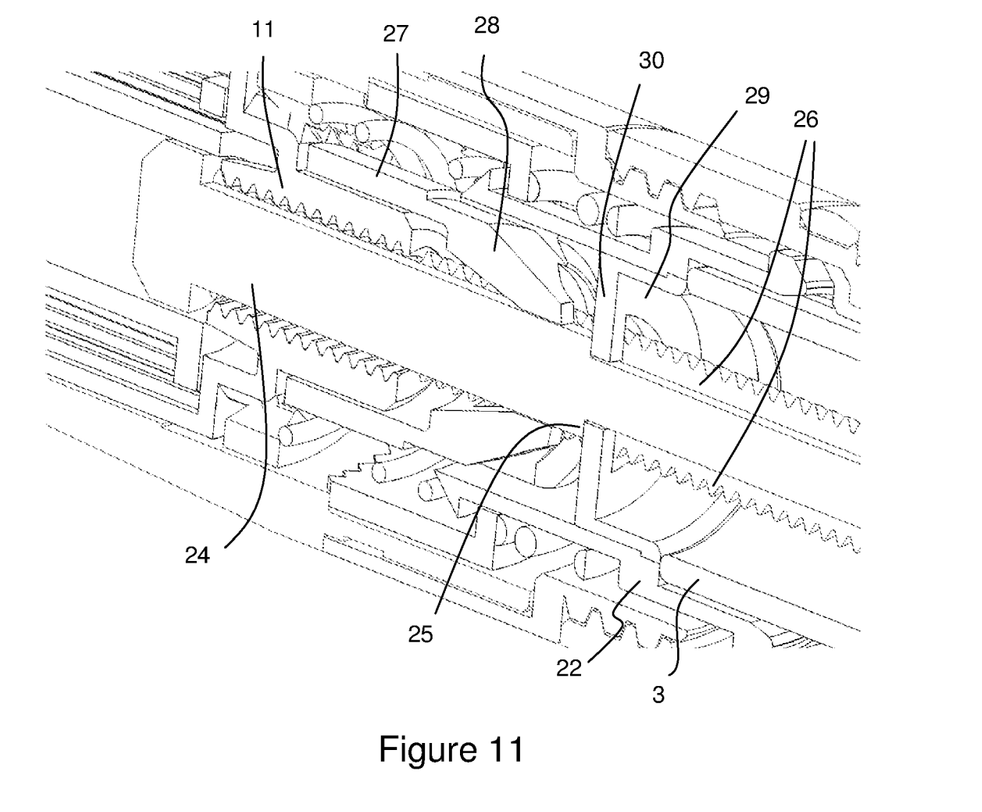
FIG. 11 illustrates a portion of the improved pen injector in the configuration of FIG. 9.

As with the known pen injector described in the background, the improved pen injector is able to deliver several doses from the same medication filled cartridge 3. During delivery of each successive dose, the leadscrew 24 is advanced further forward into the medication filled cartridge 3. This continues until the step profiles 25 meet the stop splines 30 of the stop collar 29. The stop collar 29, abutting the distal end of the cartridge, prevents further axial movement of the leadscrew 24 in the proximal direction, thereby defining the limit of movement of the leadscrew and its end cap 15. This end point is illustrated in FIGS. 9 and 11 in which it can be seen that the step profiles 25 in the axial guide tracks 26 abut the stop splines 30.

With reference again to FIGS. 1 to 4, and as has already been described, the limit of axial movement of the leadscrew in the proximal direction in the case of the prior art pen injector is defined by the point at which the enlarged end 21 of the leadscrew abuts the drive gear 11. By introducing the stop collar 29 between the drive gear 11 and the cap 15 of the leadscrew 24, the point at which the leadscrew stops with respect to the cartridge is more precisely defined. This is because manufacturing tolerances of, for example, the drive gear 11 and locking bush 27 no longer influence the stopping point of the leadscrew 24. It is therefore possible to reduce the axial length of the buffer zone required to prevent the bung from entering the tapered region of the cartridge. On average, and in comparison with the prior art pen injector, less medicine will be wasted.

While the improved pen-type injection device described refers to a leadscrew having two coaxial guide tracks, it will be understood by a person skilled in the art that any number of tracks and corresponding splines may be used, including one. While the FIGS. 5, 6, 9, 10 and 11 show the leadscrew 24 having an enlarged end at the distal end, it will be understood that this enlarged end is not required to prevent further axial motion of the leadscrew, as in the prior art.

While described above in the context of a device having a leadscrew that is rotationally fixed during delivery of a medicine, the present invention may also be applied to devices having leadscrews that rotate relative to the housing during delivery of the medicine. In such a device a drive collar and a nut may replace the drive gear 11 and the locking bush 27 of the pen injector described above. The drive collar is coupled to the torsion spring and the trigger in the same way that the drive gear of the pen injector described above couples to these components. The drive collar has one or more drive splines for engaging with the guide tracks of the leadscrew. The nut is arranged such that it can rotationally fixed when a receptacle with cartridge is attached to the housing, e.g. by means of the cartridge pressing the compression cup and thus the nut against locking features formed on an interior surface of the housing. The thread on the inner surface of the nut engages with the leadscrew thread. A reset mechanism is provided in order to allow the leadscrew to be rotated and moved axially back into the housing after injection of a final dose and removal of a spent cartridge.

The stop collar again sits within the compression cup. However, in contrast to the embodiment described with reference to FIGS. 4 to 11, the stop collar is free to rotate within the compression cup. This is necessary in order that the stop collar can rotate with the leadscrew during drug delivery, with the compression cup remaining fixed relative to the housing.

During operation, a user may select a dose, thus storing energy in the torsion spring. When the user releases the trigger, the drive collar is rotated as the torsion spring unwinds. Due to the coupling between the drive collar and the leadscrew via the drive splines and guide tracks, the leadscrew also rotates with the drive collar. The interaction of the leadscrew and the rotationally fixed nut via the complementary screw threads causes the rotating leadscrew to move axially through the rotationally fixed nut, and thereby drive medicine out of the cartridge.

The drive splines are configured to extend into the guide tracks to a depth just less than y such that the drive splines do not interfere with movement of the leadscrew in the axial direction. As a result, the step profiles formed in the guide tracks are free to move past the drive splines, but are stopped by the stop splines of the stop collar, which project into the track to a depth greater than y. The proximal limit of movement of the stop collar occurs when the stop collar abuts and is pressed against the end of the cartridge.

It will be appreciated by the person of skill in the art that further modifications may be made to the above described embodiments without departing from the scope of the present invention. For example, rather than the depth of the track(s) in the leadscrew having a step profile, a step profile may be provided in the width of the track(s), with the splines of the stop collar and of the locking bush having different widths. It will also be noted that the splines of the locking bush and the stop collar need not have the specific configurations described with reference to the figures. For example, a spline may be any projection that interacts appropriately with the guide track.

The invention claimed is:

1. An injection device comprising:
a housing;
a receptacle for receiving a medicine cartridge and configured for attachment to a proximal end of the housing;
a leadscrew having an end for engaging with a bung of a cartridge, the leadscrew having a first thread extending axially along an outer surface thereof and having at least one axially extending guide track;
a rotatable drive mechanism for engaging with said first thread or said guide track and a guiding element for engaging with the other of said first thread or said guide track, the guiding element being non-rotatable with respect to the housing at least during an injection operation, whereby rotation of the drive mechanism causes said leadscrew to move axially in a proximal direction in order to deliver a dose from the cartridge; and
a stop member located proximal to said rotatable drive mechanism and said guiding element and being engaged with the or each guide track of said leadscrew to allow relative axial movement of the leadscrew and the stop member while causing the two components to rotate together, said stop member and a profile of the or each guide track being configured to define an end stop for the leadscrew in the proximal direction.

2. An injection device according to claim 1, wherein said profile comprises a step change in the depth of the or each guide track at an intermediate position, the or each guide track having a first depth x in a proximal region of the leadscrew and a second depth y in a distal region, where x is greater than y.

3. An injection device according to claim 1, wherein the stop member comprises at least one stop spline, the or each stop spline being configured to engage with the or each guide track.

4. An injection device according to claim 2, wherein the or each stop spline of the stop member extends a distance greater than y into the or each guide track.

5. An injection device according to claim 1, wherein the rotatable drive mechanism comprises a drive gear having a second thread provided on an inner surface thereof, the leadscrew and the drive gear being rotatably coupled by means of said first and second threads, and said guiding element is a locking bush located proximal to said drive gear and comprising one or more splines for engaging with the or each guide track of the leadscrew to allow relative axial movement of the leadscrew and the locking bush while preventing relative rotational movement, the locking bush being configured to allow rotation of the leadscrew when the receptacle is disconnected from the housing and to prevent rotation when the receptacle is connected to the housing.

6. An injection device according to claim 2, wherein the or each spline of the locking bush extends a distance less than y into the or each guide track.

7. An injection device according to claim 5 and further comprising a cartridge compression cup slidably mounted within the housing and being engagable by the receptacle during attachment of the receptacle to move said locking bush from a position in which it is rotatable with respect to the housing to a position in which it is non-rotatable, and wherein said stop member is located within said compression cup.

8. An injection device according to claim 1, wherein the rotatable drive mechanism comprises a drive collar comprising one or more splines for engaging with the or each guide track such that the drive collar and leadscrew rotate together, and the guiding element is a nut, said nut having a second thread on an inner surface thereof and the leadscrew and the nut being rotatably coupled by means of said first and second threads.

9. An injection device according to claim 8 and further comprising a cartridge compression cup slidably mounted within the housing and being engagable by the receptacle during attachment of the receptacle to move said nut from a position in which the nut is rotatable with respect to the housing to a position in which the nut is non-rotatable, and wherein said stop member is located within said compression cup.

10. An injection device according to claim 9, wherein said stop member is rotatable within said compression cup.

11. An injection device according to claim 2, wherein the or each drive spline of the drive collar extends a distance less than y into the or each guide track.

12. An injection device according to claim 1, wherein a proximal end position of the stop member is defined by abutment of the stop member with an attached cartridge.

13. An injection device according to claim 1, further comprising a torsion spring coupled to said rotatable drive mechanism in order to rotate the drive mechanism within the housing.

14. An injection device according to claim 1, wherein said stop member is a stop collar.

15. An injection device comprising:

a housing;

a receptacle for receiving a medicine cartridge and configured for attachment to a proximal end of the housing;

a leadscrew having an end for engaging with a bung of a cartridge, the leadscrew having a first thread extending axially along an outer surface thereof and having at least one axially extending guide track;

a drive gear having a second thread on an inner surface thereof, the leadscrew and the drive gear being rotatably coupled by means of said first and second threads;

a drive mechanism for causing relative rotation of said leadscrew and said drive gear in order to deliver a dose from the cartridge;

a locking bush located proximal to said drive gear and being engaged with the or each guide track of the leadscrew to allow relative axial movement of the leadscrew and the locking bush while preventing relative rotational movement, the locking bush being configured to allow rotation of the leadscrew when the receptacle is disconnected from the housing and to prevent rotation when the receptacle is connected to the housing; and a stop member located proximal to said locking bush and being engaged with the or each guide track of said leadscrew to allow relative axial movement of the leadscrew and the stop member while allowing the two components to rotate together, said stop collar and a profile of the or each guide track being configured to define an end stop for the leadscrew in the proximal direction.

* * * * *